US012440363B2

(12) United States Patent
Brass et al.

(10) Patent No.: US 12,440,363 B2
(45) Date of Patent: Oct. 14, 2025

(54) FOOT ORTHOSIS WITH SWIVEL JOINT FOR CORRECTING FOOT MALPOSITIONS

(71) Applicant: LUDWIG BERTRAM GMBH, Isernhagen (DE)

(72) Inventors: Manfred Brass, Grünwald (DE); Joerg Ostenrieder, Ebenhausen (DE)

(73) Assignee: LUDWIG BERTRAM GMBH, Isernhagen (DE)

( * ) Notice: Subject to any disclaimer, the term of this patent is extended or adjusted under 35 U.S.C. 154(b) by 115 days.

(21) Appl. No.: 18/551,757

(22) PCT Filed: Mar. 22, 2022

(86) PCT No.: PCT/EP2022/057525
§ 371 (c)(1),
(2) Date: Sep. 21, 2023

(87) PCT Pub. No.: WO2022/200369
PCT Pub. Date: Sep. 29, 2022

(65) Prior Publication Data
US 2024/0173160 A1 May 30, 2024

(30) Foreign Application Priority Data
Mar. 22, 2021 (DE) ......................... 102021107084.8

(51) Int. Cl.
*A61F 5/01* (2006.01)

(52) U.S. Cl.
CPC .................................. *A61F 5/019* (2013.01)

(58) Field of Classification Search
CPC .... A61F 5/019; A61F 5/01; A61F 5/00; A61F 5/0195
See application file for complete search history.

(56) References Cited

U.S. PATENT DOCUMENTS 1,213,786 A 1/1917 Wilms
7,322,951 B2 1/2008 Reinhardt
(Continued)

FOREIGN PATENT DOCUMENTS

DE 10 2004 008909 A1 9/2005
DE 102 40 121 B4 9/2010

OTHER PUBLICATIONS

German Search Report issued for the corresponding German application DE 10 2021 107 084.8 14 pages, dated Dec. 21, 2021.
(Continued)

*Primary Examiner* — Tarla R Patel
(74) *Attorney, Agent, or Firm* — Ruggiero McAllister & McMahon LLC

(57) ABSTRACT

A foot orthosis for correcting foot malpositions, in particular for treating hallux valgus, comprising a toe splint configured to be fastened to a toe and a metatarsal splint configured to be fastened to a metatarsal region of the foot, each of which are pivotably connected relative to one another by means of a swivel joint When the foot orthosis is fastened to the foot, the foot orthosis is configured to exert a first corrective force on the toe via the toe splint and to exert a second corrective force on a metatarsophalangeal joint via the swivel joint in the opposite direction to the first corrective force The swivel joint is provided with a recess which extends along a swivel axis of the swivel joint and is designed such that, when fastened to the foot, a sideways protruding section of the metatarsophalangeal joint is received in the recess.

15 Claims, 8 Drawing Sheets

(56) References Cited

U.S. PATENT DOCUMENTS

| | | | | |
|---|---|---|---|---|
| 7,396,338 | B2 * | 7/2008 | Huber | A61F 5/10 128/893 |
| 2006/0155233 | A1 | 7/2006 | Huber et al. | |
| 2016/0242944 | A1 | 8/2016 | Ciesielski et al. | |
| 2019/0133803 | A1 | 5/2019 | Kise et al. | |

OTHER PUBLICATIONS

International Search Report and Written Opinion for corresponding International (PCT) application PCT/EP2022/057525, 15 pages, dated Jul. 11, 2022.

* cited by examiner

FOOT ORTHOSIS WITH SWIVEL JOINT FOR CORRECTING FOOT MALPOSITIONS

CROSS REFERENCE TO RELATED APPLICATIONS

This application is a national stage U.S. patent application of International Application No. PCT/EP2022/057525, filed on Mar. 22, 2022, and claims foreign priority to German Patent Application No. DE 10 2021 107 084.8, filed on Mar. 22, 2021, the entirety of each of which is incorporated herein by reference.

TECHNICAL FIELD

A foot orthosis for correcting malpositions of a foot, in particular for treating hallux valgus.

TECHNOLOGICAL BACKGROUND

Pathological malpositions in the metatarsal and forefoot area of a patient can have various causes, such as genetic predisposition, wearing wrong footwear, especially shoes that are too tight or high-heeled, or a flattening of the longitudinal and transverse arch as a result of instability of the connective tissue in the metatarsal area. In particular, malpositioning of the big toe in the metatarsophalangeal joint, also known as hallux valgus, is gaining in importance due to steadily increasing number of cases.

Hallux valgus emerges from the metatarsophalangeal joint of the big toe being pulled in the direction of the inside of the foot by muscle traction. This causes the first metatarsal to protrude from the inside of the foot as a ball-shaped protrusion at the metatarsophalangeal joint, which is referred to as pseudoexostosis. In medical literature, the ball-shaped protrusion is also described as a protrusion in the area of the metatarsophalangeal joint or as a swelling occurring in the bunion area, which may lead to painful infections of the protruding toe ball as hallux valgus progresses. In addition, hallux valgus is often accompanied by a change in the length and direction of traction of tendons, which can further exacerbate the deformity over time. As a result, arthrosis of the metatarsophalangeal joint of the big toe develops, which has to be treated surgically in advanced stages.

To stop or counteract the disease process, in addition to surgical interventions, the use of conservative therapy methods is known. For example, the use of tape bandages or orthoses is known for treating the foot in a resting position. Due to the required resting position of the foot during therapy, these are mainly used at night.

Furthermore, orthoses are known which, in a state fastened to the foot, allow a splinted big toe to move along its flexion-extension direction. For example, DE 102 40 121 B4 discloses an orthopedic device in the form of a hinged bending splint which is articulated about a flexion-extension movement axis of a toe to be corrected. For this purpose, the hinged bending splint is provided with a joint resting against the inner side of the foot and with two bending legs extending from the joint along the inner side of the foot. For fastening the hinged bending splint to the foot, a first bending leg is fastened to the toe via a first bandage and a second bending leg is fastened to the metatarsal via a second bandage.

SUMMARY

Described is a foot orthosis for correcting malpositions, in particular for treating hallux valgus, which in particular ensures effective therapeutic treatment and at the same time has a compact design and is comfortable to wear.

Accordingly, a foot orthosis is provided for correcting foot malpositions, in particular for treating or preventing hallux valgus. The foot orthosis comprises a toe splint configured to be fastened to a toe and a metatarsal splint configured to be fastened to a metatarsal region of the foot which are pivotably connected relative to one another by means of a swivel joint. The foot orthosis is configured to, in a fastened state in which the foot orthosis is properly fastened to the foot, exert a first corrective force on the toe via the toe splint and to exert a second corrective force on a metatarsophalangeal joint via the swivel joint in the opposite direction to the first corrective force. The swivel joint is provided with a recess which extends along a swivel axis or pivot axis of the swivel joint and which is designed such that, in the state fastened to the foot, a sideways or laterally protruding section of the metatarsophalangeal joint is received in the recess.

In the foot orthosis, in addition to the first corrective force exerted on the toe, the second corrective force is exerted on the metatarsophalangeal joint via the swivel joint. By doing so, a particularly effective therapeutic effect may be achieved. This is because the design of the foot orthosis may simultaneously have a therapeutic effect on a valgus position of the toe and on a varus position of the metatarsophalangeal joint. Thus, symptoms and cause of the foot malposition may be treated simultaneously. The corrective forces acting on the foot and the associated therapeutic effects are described in more detail below in connection with the related components of the foot orthosis.

In the context of the present disclosure, it has been found that the sideways protruding section of the metatarsophalangeal joint is sensitive and particularly pressure sensitive, in particular in the presence of pseudoexostosis as it may occur in hallux valgus. In order to take these circumstances into account, the foot orthosis is equipped with the swivel joint provided with the recess in which the sideways protruding section of the metatarsophalangeal is at least partially received when the foot orthosis is worn. By this configuration, the foot orthosis is prevented from contacting a distal end of the sideways protruding section of the metatarsophalangeal joint and from directly exerting forces thereon. Thus, compared to known orthoses that contact and directly exert forces on the sideways protruding section of the metatarsophalangeal joint, the load exerted on the sensitive section of the metatarsophalangeal joint can be reduced during use of the foot orthosis. In other words, the structural configuration of the swivel joint enables the foot orthosis to reduce or avoid applying forces on pressure-sensitive regions of the foot.

Further, the configuration of the swivel joint allows the foot orthosis to be kept particularly close to the foot. Also its extension in the foot width direction can be reduced. This particularly applies to those sections of the foot orthosis which, in the fastened state of the foot orthosis, are arranged sideways to the metatarsophalangeal joint of its wearer. Accordingly, the swivel joint may contribute to a compact design of the foot orthosis. Wearing the foot orthosis in conventional footwear can thus be significantly more comfortable for a patient compared to known devices, in particular due to the thus achieved compact design.

The foot orthosis is intended and configured for treating, counteracting and/or preventing pathological foot malpositions, in particular malpositions of a toe and/or its metatarsophalangeal joint. In particular, the foot orthosis may be used for preventing or treating hallux valgus, but is not limited to this application. Accordingly, the foot orthosis is intended and configured to be fastened to a patient's foot and, in the state fastened to the foot, to therapeutically act on the foot, in particular on the toe and/or the metatarsophalangeal joint.

In the present disclosure, the term "in a/the state properly fastened to the foot", herein also referred to as "in the fastened state", refers to a state in which the foot orthosis is properly fastened to a patient's foot and accordingly produces a desired therapeutic effect for correcting or preventing malpositions. The foot orthosis may be foot-specifically designed for a left or right foot of a patient. In other words, the foot orthosis may be intended and designed for use on either the left or right foot of the patient. A foot orthosis intended for the left foot may be mirror symmetric to a foot orthosis intended for the right foot of a patient.

The foot orthosis is designed to, in the fastened state, exert corrective forces on the foot. In the present disclosure, the term "corrective forces" refers to forces that have a therapeutic effect on the foot to be treated. In particular, the corrective forces cause those parts of the foot affected by the malposition to be positioned into or towards an anatomically correct or intended position to achieve a desired therapeutic effect.

The foot orthosis is configured to, in the fastened state on the patient's foot, exert, in particular directly exert, at least the first and the second corrective force on the foot to be treated by means of the toe splint and the swivel joint. By this design, the foot orthosis differs substantially from known devices which, intentionally or unintentionally, shield a metatarsophalangeal joint and the ball of the toe associated therewith or a pathological pseudoexostosis caused by the malposition from external forces, in particular from forces acting on the foot through the device. As set forth above, in the context of the present disclosure, it has been found that a particularly effective therapeutic effect can be achieved if the foot orthosis, in addition to the first corrective force acting on the toe, also exerts the second corrective force acting on the metatarsophalangeal joint by means of the swivel joint. The resulting interaction of corrective forces exerted on the foot can be particularly beneficial in the treatment of hallux valgus.

In the following, in connection with the toe splint, it is generally referred to a toe of the foot for the sake of simplicity which can mean the big toe of the foot to be treated. However, the foot orthosis is not limited to this application such that the term "toe" may also relate to, for example, the little toe. In connection with the swivel joint, accordingly, it is generally referred to a metatarsophalangeal joint which can mean the metatarsophalangeal joint of the big toe. Yet, the foot orthosis is not limited to this application. Alternatively, the term metatarsophalangeal joint may refer to, for example, the metatarsophalangeal joint of the little toe.

In the present disclosure, for specifying the foot orthosis, in particular with respect to the foot to be treated, a reference system is used which is oriented to the midline or medial plane of a patient's body, as is common in anatomy. Thus, the position and direction of each component of the foot orthosis in the fastened state may be indicated with respect to the foot received in the foot orthosis. Accordingly, the term "medial" refers to a direction or side of the foot orthosis that points toward a medial plane of the wearer's body. In anatomy, the term "medial plane", also known as "midsagittal plane", generally refers to an anatomical plane that divides the body into two symmetrical parts. Accordingly, when describing a foot orthosis, the term "in medial direction" means a direction pointing from the patient's foot to be treated towards his other foot. In this sense, the term "lateral" refers to a direction or side of the foot orthosis that points away from the medial plane of the wearer's body. Accordingly, when describing a foot orthosis fastened to one foot of the wearer, the term "lateral" means in a direction facing away from the other foot of the wearer.

For interacting with the metatarsophalangeal joint of the foot to be treated, i.e. for exerting the second corrective force, the orthosis is provided with the swivel joint, which in particular is provided in the form of a hollow trunnion swivel joint or hubless joint. In the present disclosure, the term "swivel joint" refers to a joint, via which two components are rotatably mounted, wherein the two components are pivotable and engaged relative to one another. In the context of the present disclosure, the term "hollow trunnion swivel joint", which may also be referred to as a hubless swivel joint, relates to a joint which along its swivel axis is at least partially provided with a hollow shape, i.e. is hollow, to form the recess. In other words, the components forming the swivel joint are provided hollow along the swivel axis such that the swivel joint is provided with the recess or through hole around and along its swivel axis.

The swivel joint may comprise components which are pivotable relative to each other about the swivel axis and which are guided relative to each other in the swivel joint. The region provided for guiding the components, which may be provided by bearing points and/or bearing surfaces, in particular by contact surfaces and/or sliding surfaces, can be arranged circumferentially around the swivel axis and spaced apart therefrom.

The region provided for guiding the components of the swivel joint may be arranged at a distance from, i.e. spaced apart from, the swivel axis by a guiding radius. The guiding radius may in particular indicate an average radius of the region provided for guiding the components of the swivel joint about the swivel axis. The guiding radius may lie in a region of an outer radius of the swivel joint, wherein the outer radius describes a length of extension of the swivel joint in the radial direction. The guiding radius may be at least 70% of the outer radius of the swivel joint. In particular, the guiding radius may be at least 80% or at least 90% of the outer radius of the swivel joint.

The swivel joint may be provided in the form of a ring joint in which the guiding surface or guiding surfaces between the components of the swivel joint, which are pivotably mounted relative to one another, is/are arranged ring-shaped around the joint or swivel axis of the swivel joint. In this way, the swivel joint can be particularly robust with respect to bending forces and bending moments. As a result, the swivel joint can transmit high forces and moments and apply them to the foot to be treated, while at the same time maintaining a compact design of the foot orthosis.

The recess may be provided in the form of a recess that is open on at least one side. In the fastened state, the recess can be open in the direction of the foot. Alternatively, the recess may be provided in the form of a through hole, in particular in the form of a through hole extending along the swivel axis. In other words, the recess may extend along the entire width or thickness of the swivel joint. In the context of the present disclosure, the terms "width" and "thickness" of the swivel joint refer to an extension of the swivel joint along the swivel axis. The swivel joint may have a width, in particular a maximum width, of 1.0 cm or 0.6 cm.

The foot orthosis may be provided such that, in the fastened state, the sideways protruding section of the metatarsophalangeal joint extends along at least 50% or at least 70% or at least 80% of the maximum width of the swivel joint. Furthermore, the foot orthosis may be provided such that, in the fastened state, the sideways protruding section of the metatarsophalangeal joint protrudes or substantially protrudes through the recess, in particular through the through hole, along the swivel axis. In this way, the foot orthosis can be kept particularly close to the foot.

The swivel joint may comprise a side wall which delimits or confines the recess and which is arranged circumferentially around the swivel axis. The side wall may have a minimum radius of curvature of 1 mm or 2 mm or 5 mm. In other words, the swivel joint may be designed such that the side wall at no point or at no section has a radius of curvature that is less than the minimum radius of curvature. The reciprocal value of the radius of curvature corresponds to the curvature of the side wall, in particular to a curvature of an inner surface of the side wall facing the recess. In this way, it may be ensured that the region of the swivel joint adjacent to the sideways protruding section of the metatarsophalangeal joint is not provided with sharp edges in order to prevent pressure peaks on the patient's foot when wearing the foot orthosis.

The recess may have a minimum diameter, in particular along a direction transverse to the swivel axis or around the swivel axis, of at least 1.5 cm or at least 2.0 cm or at least 2.5 cm. For example, the recess may have a circular or elliptical shape in cross-section along the swivel axis with a minimum diameter of at least 1.5 cm or at least 2.0 cm or at least 2.5 cm. For example, the diameter may be 3.0 cm or substantially 3.0 cm.

The shape of the recess, in particular its cross-sectional shape and diameter, may be adapted to the foot to be treated, in particular to the shape of the sideways protruding section of the metatarsophalangeal joint. This may be done on the basis of orthopedic or physiological classification specific to the user group. For example, foot orthoses can be provided in this way for user groups with feet of different sizes and/or user groups with sideways protruding sections of the metatarsophalangeal joint, in particular with pseudoexostosis, of different sizes.

As set forth above, the toe splint and the metatarsal splint are pivotably coupled relative to one another by means of the swivel joint. By this configuration it is enabled that, when wearing the foot orthosis, a toe splinted by the foot orthosis can be moved relative to the metatarsus along its flexion-extension movement direction. In other words, the foot orthosis and thus the swivel joint unit may be configured such that, in the fastened state, the toe to be treated is movable relative to the metatarsophalangeal joint in the flexion-extension directions. Accordingly, the swivel joint may be provided and configured such that, in the fastened state, the swivel axis of the swivel joint is parallel or substantially parallel to a base joint axis of the metatarsophalangeal joint, in particular is parallel or substantially parallel to the flexion-extension movement axis of the metatarsophalangeal joint. More specifically, the swivel axis of the swivel joint may coincide with, i.e. be aligned with, or substantially coincide with the base joint axis of the metatarsophalangeal joint, in particular with the flexion-extension movement axis. Alternatively or additionally, the swivel axis of the swivel joint may be arranged parallel or substantially parallel to the first and/or the second corrective force.

Furthermore, the swivel joint may be configured to transmit shearing and/or bending forces between the toe splint and the metatarsal splint to exert the first and/or the second corrective force on the foot. In other words, the swivel joint of the foot orthosis may be configured to, in the fastened state, transmit forces parallel to the corrective forces, in particular shearing or bending forces, to generate the first and/or the second corrective force. For doing so, the swivel joint may be provided to transmit forces between the metatarsal splint and the toe splint in the direction of the swivel axis of the swivel joint. In particular, the swivel joint may be provided such that bending forces are transmitted between the metatarsal splint and the toe splint along a longitudinal extension of the foot orthosis, which extends from the metatarsal splint via the swivel joint to the toe splint and which thus essentially equals in the direction of the longitudinal direction of the foot when the foot orthosis is fastened to the foot. The bending forces may extend in the medial-lateral direction and/or lateral-medial direction. The thus transmitted forces along the splint may induce the corrective forces to be exerted on the foot by the foot orthosis.

In this way, the foot orthosis provides a splinted toe with sufficient freedom of movement so that the foot orthosis supports the foot in its natural walking movement and at the same time has a therapeutic effect on it. This allows the foot orthosis to be used in the patient's everyday life, which increases the patient's willingness to wear the foot orthosis and thus the acceptance and success of the therapeutic treatment.

The swivel joint may be designed such that, in the fastened state of the foot orthosis, relative pivoting movement between the toe splint and the metatarsal splint is locked about an axis arranged obliquely or orthogonally to the swivel axis. The swivel joint may be designed such that relative pivoting movement is permitted only about the swivel axis. In other words, the swivel joint may be structurally provided such that pivoting movement about the swivel axis is released, while pivoting movement about an axis oblique or perpendicular to the swivel axis is locked. In this way, a simple and compact design of the swivel joint may be provided.

The foot orthosis can be provided such that, in the fastened state, the swivel joint is arranged on a side of the foot. In particular, in the fastened state, the swivel joint may be arranged on a medial side of the foot. In other words, in the fastened state, the swivel joint may be arranged on the inner side of the foot, i.e. medially on the foot, wherein in particular the toe splint and the metatarsal splint may be arranged medially.

The swivel joint may be formed or constituted by structurally engaging regions of the toe splint and the metatarsal splint. Specifically, the swivel joint may be formed or constituted by structurally engaging end regions of the toe splint and the metatarsal splint. The swivel joint may at least partly be provided by the engaged regions of the toe splint and the metatarsal splint, or may entirely be constituted by the engaged regions of the toe splint and the metatarsal splint. The section of the toe splint and/or the metatarsal splint forming the swivel joint may be an integral part of the toe splint and/or the metatarsal splint. In this way, a simple design of the foot orthosis may be ensured by using a small number of components.

In a further development, the swivel joint may comprise a first joint element coupled to the toe splint, in particular integrally connected or adhesively bonded thereto, and a correspondingly designed second joint element which is engaged with the first joint element and which is coupled to the ball segment, in particular integrally connected or adhesively bonded thereto. The first joint element and the second joint element may be form-fittingly engaged along the swivel axis, in particular in a first direction and a second opposite direction along the swivel axis, and/or transversely to the swivel axis of the swivel joint.

The swivel joint may be designed such that, in the fastened state, the second joint element is arranged between the foot and the first joint element. In this way, it may be prevented that during a flexing movement of the splinted toe, the section of the swivel joint lying against the foot is pivoted relative to the sideways protruding section of the metatarsophalangeal joint. This may increase wearing comfort of the foot orthosis.

The second joint element may form a joint pin of the swivel joint which guides movement around the swivel axis of a joint ring formed by the first joint element. Alternatively, the first joint element may form the joint pin and the second joint element may form the joint ring. The joint pin can be provided in the form of a hollow pin, the hollow section of which constitutes the recess. The joint ring and the joint pin may be designed and engaged in such that they are form-fittingly engaged along the swivel axis, in particular in the first direction and the opposite second direction along the swivel axis.

The joint pin, as regards is geometric design, may be adapted to the shape of the joint ring. The joint ring may comprise a first guiding surface which may be formed correspondingly to a second guiding surface of the joint pin. The first and the second guiding surface, which in particular constitute sliding and bearing surfaces, may be engaged with one another, in particular substantially without clearance or with a predetermined clearance. During pivoting movement, the first and the second guiding surfaces may be moved relative to each other.

The first guiding surface of the joint ring may be or comprise a surface which is oriented radially inward, i.e. which faces the swivel axis. The first guiding surface may extend circumferentially around the swivel axis and may be arranged annularly about the swivel axis.

The second guiding surface of the joint pin may be or comprise a surface oriented radially outward which in particular may constitute a sideways surface of the joint pin. The second guiding surface may extend circumferentially around the swivel axis and may be arranged annularly about the swivel axis.

Further, the joint pin may comprise a circumferential radial shoulder at a distal and/or proximal end, wherein the shoulder, in particular by way of a snap hook, provides a form-fitting connection or undercut securing between the joint ring and joint pin in direction of the swivel axis. In order to provide a substantially flat outer contour or outer surface on the medial outer side of the foot orthosis, the radial shoulder may be received in a correspondingly designed receptacle or recess on the joint ring. Alternatively or additionally, a separate locking ring may be provided which can be inserted into a correspondingly designed groove at the joint ring or joint pin. The radial shoulder may extend along the swivel axis in such a way that it overlaps the joint ring in the axial direction of the swivel joint and in particular engages around the joint ring. By this arrangement, the foot to be treated can be prevented from coming into contact with the receiving groove or the joint ring, thereby increasing comfort for a patient.

The first and the second guiding surface may comprise at least one axially delimiting side surface, for example two opposing side surfaces, to provide the form-fitting connection along the swivel axis. By this configuration, forces, in particular bending forces, in direction of the swivel axis of the swivel joint can be transmitted between the components.

According to one configuration, the joint pin, in particular the second joint element, or the joint ring may be provided with a receiving groove which is arranged circumferentially around the swivel axis and which extends in radial direction, i.e. towards the swivel axis. The receiving groove may be delimited, in particular sideways delimited, in the axial direction along the swivel axis. The inner surfaces of the receiving groove may constitute a contact and sliding surface, i.e. the first or the second guiding surface. In other words, the receiving groove may form a substantially U-shaped contact or sliding surface in longitudinal section along the swivel axis. The correspondingly designed guiding surface may be provided at a connecting ring correspondingly designed to the receiving groove. The connecting ring may be guided in the receiving groove and may be rotated relative to the receiving groove in the circumferential direction about the swivel axis. In the engaged state of the receiving groove and the connecting ring, the connecting ring is arranged in the receiving groove such that the first joint element and the second joint element are form-fittingly connected to one another in axial direction of the swivel axis.

In other words, the joint pin may be provided with a receiving groove in which a correspondingly designed connecting ring of the joint ring is guided. Alternatively, the joint ring may be provided with the receiving groove in which a correspondingly designed connecting ring of the joint pin is guided.

Further, the foot orthosis includes the toe splint. The toe splint may be configured and intended to be brought into engagement with the toe of the foot in a predefined position to provide a force-transmitting coupling between the toe and the toe splint in the fastened state. Accordingly, in the fastened state, the toe splint is held in a desired position. The toe splint is further intended to apply the first corrective force to the toe when being fastened to the foot. The first corrective force may act on the toe in the medial direction, while the corrective force exerted by the swivel joint may act in the lateral direction.

The foot orthosis further comprises the metatarsal splint. The metatarsal splint may be intended to exert a holding force on the metatarsus when being fastened to the foot. The holding force may act in a direction parallel to the first corrective force and, together with the first corrective force, may form a counterforce to the second corrective force. The interaction of these forces may reliably keep the foot orthosis stable on the foot to be treated in a position intended for therapeutic treatment. By this configuration, the foot orthosis may be fastened to the foot to be treated with the mode of action of a tension clamp or clip.

In a further development, the holding force exerted by the metatarsal splint may have a therapeutic effect on the foot to be treated, contributing in particular to the therapeutic effect of the first and second corrective force and/or providing a further therapeutic effect distinct therefrom. For example, the further corrective force exerted by the metatarsal splint may cause the arch of the foot to straighten up. To support this effect, the foot orthosis may further comprise a foot cushion, also referred to as pad, which is arranged below the sole of the foot in the metatarsal region, in particular below the arch of the foot. Such a foot cushion may be detachably connected to the metatarsal splint.

The toe splint and/or the metatarsal splint may comprise a bracket or clamp element extending along the splinted toe or along the splinted metatarsal.

In the context of the present disclosure and generally, the term "bracket element" or "clamp element" refers to a component that is designed and provided to receive and transmit different loads, such as longitudinal forces, transverse forces, shear forces, bending forces, bending moments, torsional moments, etc. As such, a bracket or clamp element is configured to receive and transmit not only tensile forces but also compressive forces along its longitudinal axis and transverse forces transverse to its extension axis, in particular transvers to its longitudinal axis. This structural configuration substantially distinguishes a bracket or clamp from a bandage, which is provided for the transmission of tensile forces but not for the transmission of compressive and/or transverse forces.

Accordingly, the bracket element of the toe splint and/or of the metatarsal splint may be configured, in the fastened state, to receive and transmit shearing forces and/or bending forces, in particular in direction of the first corrective force to the foot and/or between the joint unit and the toe to be treated, in order to exert the first corrective force on the toe and/or to exert the holding force on the metatarsal.

In a further development, the bracket element of the toe splint and/or of the metatarsal splint may be provided in the form of a clamping bracket or bending spring. By this configuration, the first corrective force and/or the second corrective force and/or the holding force may be provided in the form of a clamping force induced by elastic deformation of the bracket element of the toe splint and/or the metatarsal splint.

Accordingly, the foot orthosis may be configured such that, in the fastened, the swivel joint transmits bending forces parallel to the first or the second corrective force between the metatarsal splint and the toe splint, wherein the first corrective force and/or the second corrective force and/or the holding force are provided in the form of a bending force induced by an elastic deformation of the toe splint and the metatarsal splint. In this way, it may be ensured that the corrective forces are persistently applied to the toe and the metatarsophalangeal joint when the foot orthosis is worn, i.e., even when the toe moves relative to the metatarsal, as is the case, for example, when walking.

The foot orthosis may be designed such that, in a state of the foot orthosis uncoupled from the foot, i.e. in a state in which the foot orthosis is not in engagement with the foot to be treated and thus is detached from the foot, the foot orthosis, in particular the bracket element of the toe splint and/or the metatarsal splint, is arranged in a rest position in which the foot orthosis, in particular the bracket element of the toe splint and/or the metatarsal splint, is not elastically deformed. In contrast, in the state of the foot orthosis fastened to the foot, the foot orthosis, in particular the bracket element of the toe splint and/or the metatarsal splint, may be arranged in a clamping position in which the foot orthosis, in particular the bracket element of the toe splint and/or the metatarsal splint, is elastically deformed. The bracket element of the toe splint and/or the metatarsal splint, specifically an end portion of the bracket element, may be elastically deflected in the clamping position relative to the rest position in a direction opposite to the first corrective force. For example, the bracket element of the toe splint and/or the metatarsal splint, in particular its end portion, may be deflected or translationally displaced in the clamping position relative to the rest position by at least 0.2 cm, for example by at least 0.3 cm or at least 0.5 cm or at least 1.0 cm, specifically along the direction opposite to the first corrective force.

In the clamping position, the bracket element of the toe splint and/or the metatarsal splint may be loaded or pre-loaded by its elastic deformation in the direction of the first corrective force. The tensioning force or bending force acting on the bracket element of the toe splint or the metatarsal splint may correspond to the first corrective force and/or the holding force.

In order to couple the bracket element of the toe splint or the metatarsal splint in a force-transmitting manner to the toe or the metatarsal to be splinted, the bracket element may be designed such that it at least partially embraces or engages around the toe or the metatarsal. In other words, the bracket element of the toe splint and/or the metatarsal splint may be configured such that it at least partially engages around the toe or the metatarsal in the fastened state. In the context of the present disclosure, the term "engaging around the toe or metatarsal" means that, in the fastened state, the bracket element extends around the toe along its circumferential direction or extends around the metatarsal along its circumferential direction. The bracket element can extend along the toe or metatarsal over a radian of at least ½ π rad around the longitudinal axis of the toe or the metatarsal. That is, the bracket element extends circumferentially along at least a quarter or a half of the circumference of a toe or the metatarsal.

With regard to the geometric design, the bracket element may be plate-shaped and/or shell-shaped. For example, with regard to its geometric design, the bracket element may be belt- or band-shaped and particularly may be bending resistant. Accordingly, the bracket element may be provided with a contact surface for the toe and an opposite support surface. In the fastened state of the foot orthosis, the contact surface of the bracket element may lie against the toe, in particular may touch the toe. The contact surface may be provided in the form of a turning surface, the orientation of which, i.e. whose surface normal, changes along the longitudinal axis of the toe and can point to the longitudinal axis of the toe. By this configuration, the contact surface and thus also the bracket element may extend along a helical line around the longitudinal axis of the toe.

According to one embodiment, the bracket element may be designed such that the size of the bracket element, specifically its span along the transverse axis of the foot orthosis, can be adapted to the size of the foot to be treated. For doing so, the bracket element may, for example, be made of multiple parts, wherein a corresponding plurality of parts of the bracket element may be coupled to one another and may be displaceable relative to one another along the transverse axis of the foot orthosis. The coupling between the plurality of parts may be selectively locked or released to adjust the size of the bracket element. In a released state, the plurality of parts may be translationally displaceable relative to each other to set a desired relative position. Thereafter, the coupling may be locked by a force and/or a form closure such that relative translational movement between the plurality of parts is locked.

Alternatively or additionally, the bracket element of the toe splint and/or the metatarsal splint may extend along the toe or along the metatarsal on an inner side of the foot, specifically in the form of a bending limb, and may be fastened to the toe or the metatarsal in a force-transmitting manner by means of a support band. For doing so, the support band, which may also be referred to as a bandage, may at least partly lie against the toe or the metatarsus along its circumferential direction, wherein the support band is coupled to the bracket element so as to fix the bracket element in a form-fitting and/or force-fitting manner relative to the toe or the metatarsal. The support band may be provided in the form of a strap, a loop, a band, a belt, etc.

In the context of the present disclosure, the term "bandage" or "support band" generally refers to a component configured and intended to receive and transmit loads, in particular tensile forces. Specifically, the support band may be a loop element that is adjustable in length. Accordingly, a circumferential length of the support band may be adjustable by a user. On the one hand, this allows foot-specific adjustments and, on the other hand, may ensure an effective flow of forces. Specifically, the support bands may be tensile rigid, or substantially tensile rigid, along their circumferential direction.

Additionally or alternatively, the support bands may be elastic or elastic in sections along their circumferential direction. Specifically, the support bands may be in the form of ring tapes or loop elements that are tensile rigid and/or elastic, or elastic in sections.

The support band may lie against a lateral side of the toe or metatarsus and may exert the corrective force or holding force thereon. For doing so, the support band can be subjected to a tensile force at its end sections by means of the bracket element. In the fastened state of the foot orthosis, the support band may be arranged at least partially around the toe or the metatarsus along their circumferential direction.

In a further development of the foot orthosis, the swivel joint may be configured to, in the fastened state, transmit shear forces and/or bending forces parallel to the first or the second corrective force between the metatarsal splint and the toe splint. Thus, the swivel joint can generate the second corrective force upon interaction with the first corrective force and the holding force. In this way, the amount of the second corrective force may be varied by a user by adjusting the toe splint or the metatarsal splint, for example by adjusting the circumferential length of the support band(s).

The toe splint and/or the metatarsal splint may be made of a plastic material, in particular of thermoplastics or a thermoplastic elastomer, etc. The toe splint and/or the metatarsal splint may be manufactured by an additive manufacturing process or an injection molding process. Further, the individual components may comprise different materials, in particular different plastic materials, which can have different material properties. The use of an additive manufacturing process or an injection molding process makes it possible that the individual components are provided integrally and yet can be made of different materials and can have different material properties. In other words, the sections of the individual components consisting of different materials can be integrally or adhesively bonded to each other.

In a further development, the foot orthosis, in particular the toe splint and/or the metatarsal splint, on its/their inside, may be provided with a support layer or coating, in particular a cushioning coating, for example a cushioning polyvinyl chloride (PVC) coating or a polyurethane (PU) coating, wherein in particular the coating is softer, i.e. has a lower hardness, compared to the section of the foot orthosis carrying the coating. The coating can be applied to the inside of at least one component of the foot orthosis. The term "inside" refers to those regions of the foot orthosis that face the foot in the fastened state. The cushioning coating may be applied in an additive process in the form of a solid or gel to the inside surfaces of the foot orthosis or the limbs or splints. For example, the cushioning coating may be applied by lamination or laminating. Further, a suitable PVC material or PU material may be melted and pressed onto a splint to create the coating. Additionally or alternatively, the coating may be applied in a liquid state, in particular by dipping, doctoring, roller application, spraying, foaming or any other suitable method.

BRIEF DESCRIPTION OF THE FIGURES

Further embodiments are explained in more detail below with reference to the figures, which schematically show in.

DETAILED DESCRIPTION

Figure 1:
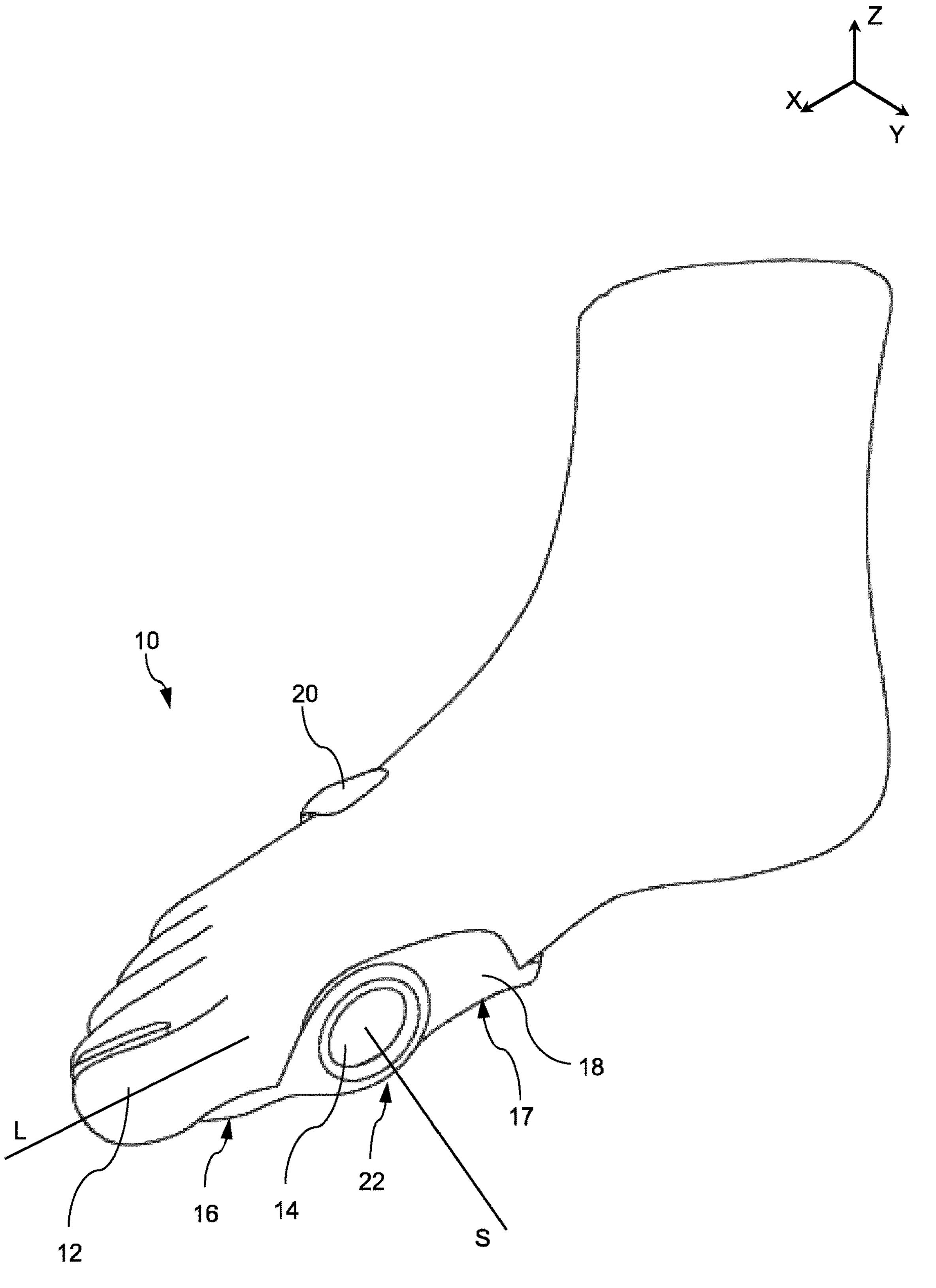
FIG. 1 a perspective view of a foot orthosis in a state fastened to a patient's foot.

In the following, embodiments are described on the basis of the Figures. In the Figures, identical, similar or similarly acting elements are denoted by identical reference numerals and a repeated description thereof may be omitted in order to avoid redundancies.

FIG. 1 shows an embodiment of a foot orthosis 10 for correcting foot malpositions. In particular, the foot orthosis 10 shown in FIG. 1 is intended and provided for treating hallux valgus, i.e. the pathological malposition of a big toe 12, also referred to as valgus position of the big toe, and of a big toe metatarsophalangeal joint 14, also referred to as *varus* position of the big toe metatarsophalangeal joint. Further, the shown foot orthosis 10 can be used for preventing hallux valgus. In the following, for simplicity reasons, the term "big toe" will be abbreviated by the term "toe" and the term "metatarsophalangeal joint of the big toe" will be abbreviated by the term "metatarsophalangeal joint of the toe".

As can be gathered from FIG. 1, the foot orthosis 10 is configured to be fastened to a foot to be treated in the manner of a clamp, in particular a tension clamp, and to be fixed thereto in a predetermined position. The foot orthosis 10 is designed and configured to, in the shown fastened state, therapeutically act on the foot by selectively applying corrective forces to the foot, in particular to a region of the toe 12 and the metatarsophalangeal joint 14, as will be further specified below.

The shown foot orthosis 10 is designed to be used on the patient's right foot. For treatment of the patient's left foot, a foot orthosis may be used that is mirror symmetric to the configuration shown in FIG. 1.

The foot orthosis 10 comprises a toe splint 16 configured to be fastened to the toe 12 and a metatarsal splint 17 configured to be fastened to a metatarsal region of the foot, wherein the metatarsal splint 17 comprises a ball segment 18 and a metatarsal segment 20. The toe splint 16 and the metatarsal splint 17 are pivotably connected relative to one another by means of a swivel joint 22. In the shown configuration, the metatarsal splint 17 is formed by the ball segment 18, which is configured to be arranged in the region of the metatarsophalangeal joint 14, and the metatarsal segment 20, which is configured to be attached to or in the region of the metatarsus.

Figure 2:
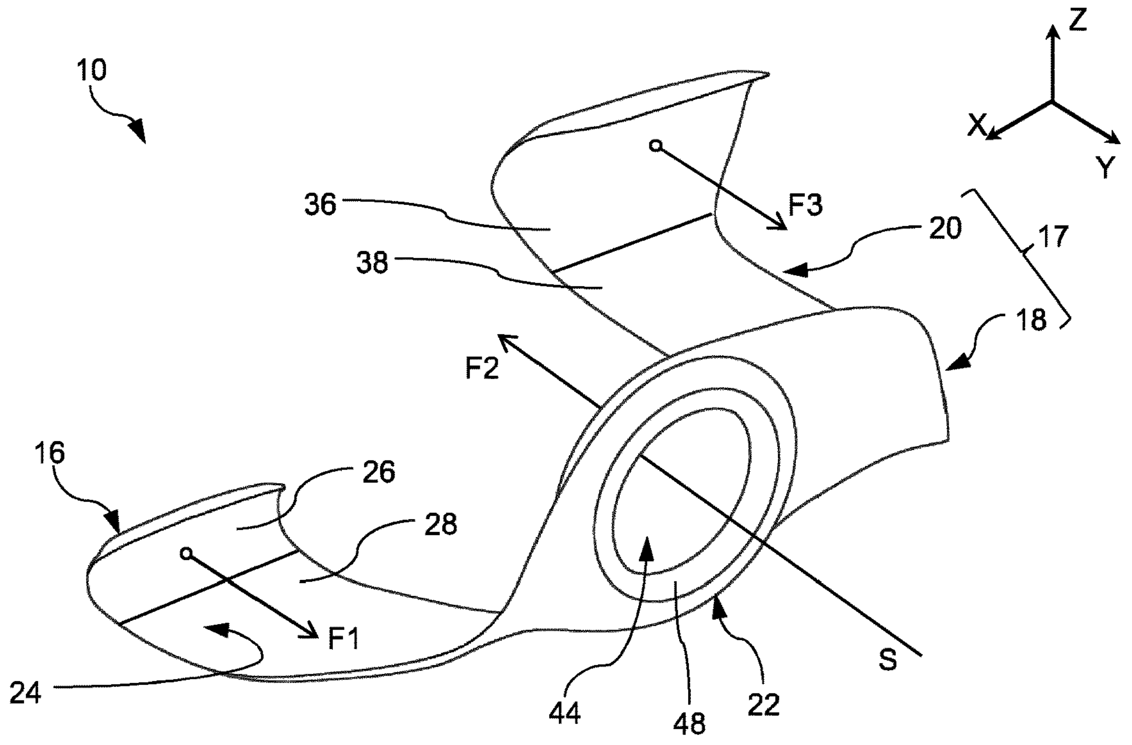
FIGS. 2 and 3 perspective views of the foot orthosis depicted in FIG. 1, in which for overview reasons the foot is not shown.

In the state fastened to the foot, as indicated in FIG. 2, the foot orthosis 10 is configured to exert a first corrective force F1 on the toe 12 via the toe splint 16, to exert a second corrective force F2 on the metatarsophalangeal joint 14 via the swivel joint 22, and to exert a holding force F3 to the metatarsus via the metatarsal splint 17. The second corrective force F2 is opposed to the first corrective force F1, in particular is parallel to and spaced apart from the first corrective force F1. The holding force F3, which may be a third corrective force, points in direction of the first corrective force F1 and is parallel to and spaced apart from the first corrective force F1.

The forces F1, F2, F3, acting on the treated foot during use of the foot orthosis 10, are illustrated in FIG. 2, in which the foot is not shown for reason of better visualization. For simplicity reasons, the corresponding forces F1, F2, F3 are shown in the form of individual vectors, wherein each of the forces, of course, is distributively exerted via a corresponding contact surface between the foot and the foot orthosis during use.

As will be specified below, the individual components of the foot orthosis 10, in particular the toe splint 16 and the metatarsal splint 17, are elastically deformable, wherein the different forces F1, F2, F3 exerted on the foot by the foot orthosis 10 are provided in the form of clamping and/or bending forces induced by elastic deformation of the foot orthosis 10. By this configuration, it may be ensured that the forces F1, F2, F3 exerted by the foot orthosis 10 are persistently applied to the foot even when the foot is moving and its shape changes during use. In this way, it may further be achieved that, upon moving the toe 12 relative to the metatarsus, the corrective force applied thereto is adjusted, for example increased, due to an increasing elastic deformation of the foot orthosis 10, in particular of the toe splint 16 and/or the metatarsal splint 17. This may improve the therapeutic effect provided by the foot orthosis.

The first corrective force F1, the second corrective force F2, and the holding force F3 are arranged parallel or substantially parallel and are spaced apart relative to each other. The first corrective force F1 and the holding force F3 point in the medial direction and are parallel or substantially parallel to a transverse axis Y of the foot orthosis 10. The second corrective force F2 points in the lateral direction. The first corrective force F1, the second corrective force F2, and the holding force F3 are further arranged orthogonal or substantially orthogonal to a longitudinal axis X and a vertical axis Z of the foot orthosis 10.

The toe splint 16 is provided in the form of a bracket or clamp, in particular in the form of a tensioning or bending clamp, which engages around, i.e. encompasses, the toe 12 in the fastened state. In the shown configuration, the toe splint 16 extends from a medial side of the foot, starting from the ball segment 18, along a lower side of the toe 12 to a lateral side of the toe 12. Thus, the toe splint 16 extends in sections, i.e. partially, along the lower side of the toe 12. Alternatively, the toe splint 16 may extend along an upper side of the toe 12. In the shown configuration, the toe splint 16 extends along the toe over a radian of one π rad around the longitudinal axis L such that the toe splint 16 extends from one side of the toe 12 and the metatarsophalangeal joint 14 to the opposite side of the toe 12, as shown in FIG. 1.

The toe splint 16 comprises a contact surface 24 for the toe 12. The contact surface 24 is provided in the form of a turning surface, the orientation of which, i.e. the surface normal of which, changes along the longitudinal toe axis L and can point to the longitudinal toe axis. By this configuration, the contact surface 24 and thus also the toe splint 16 extend along a helical line around the toe 12.

The toe splint 16 is configured to, in the fastened state, transmit shearing forces and/or bending forces in direction of the first corrective force F1 between the swivel joint 22 and the toe 12 to be treated, thereby contributing in generating the first corrective force F1.

In order to exert the first corrective force F1 on the toe 12, the toe splint 16 comprises a toe support section 26 which, in the fastened state of the foot orthosis 10, contacts a lateral side of the toe 12, i.e. a side of the toe 12 pointing in lateral direction. The toe support section 26 is formed by a distal end section of the toe splint 16. The toe splint 16 further comprises a toe base section 28 integrally coupled and adhesively bonded to the toe support section 26 and arranged adjacent thereto, as indicated by a dotted line in FIG. 2.

The toe splint 16, in particular the toe support section 26, is provided in the form of a bending spring or spring element. Thus, the first corrective force F1 is provided in the form of a clamping force or bending force induced by an elastic deformation of the toe splint 16. In other words, the toe splint 16 is provided such that, in the fastened state, the toe splint 16 is arranged in a clamping position in which the toe splint 16 is elastically deflected in a direction opposite to the first corrective force F1 with respect to a rest position of the toe splint 16 in which the toe splint 16 is arranged in a state of the foot orthosis 10 being decoupled from the foot.

Figure 4:
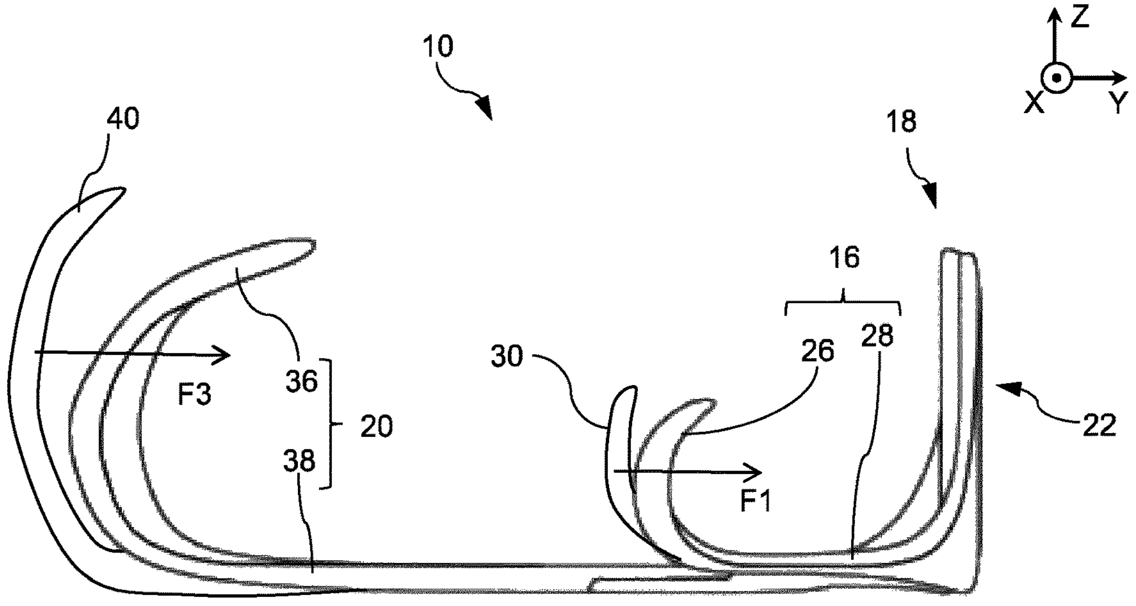
FIG. 4 to 8 different views of the foot orthosis depicted in FIGS. 1 to 3 in a state decoupled from the foot.
Figure 5:
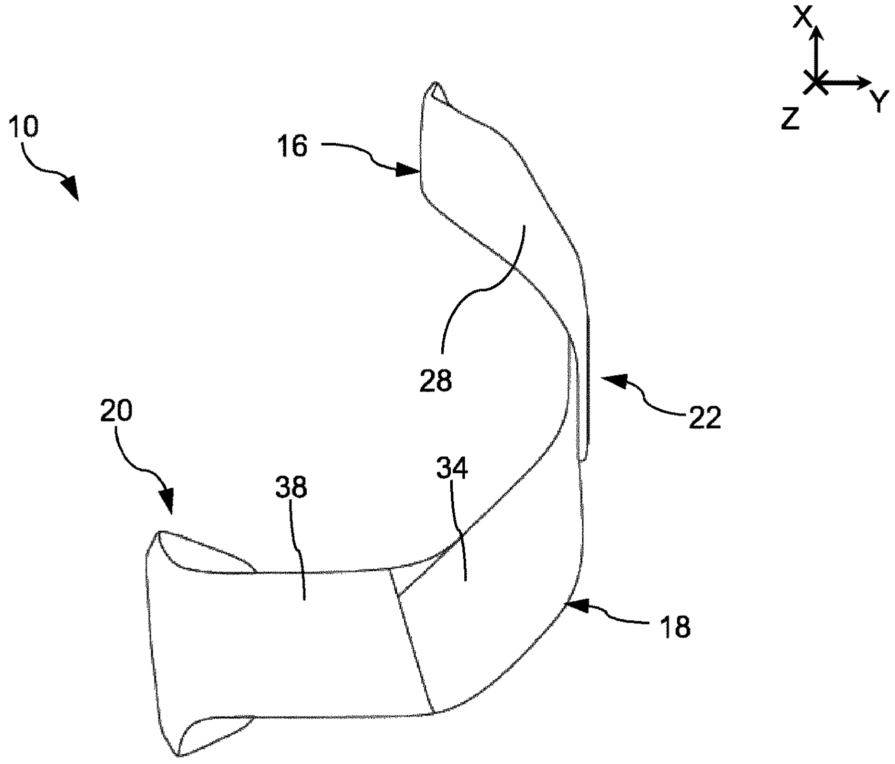
Figure 6:
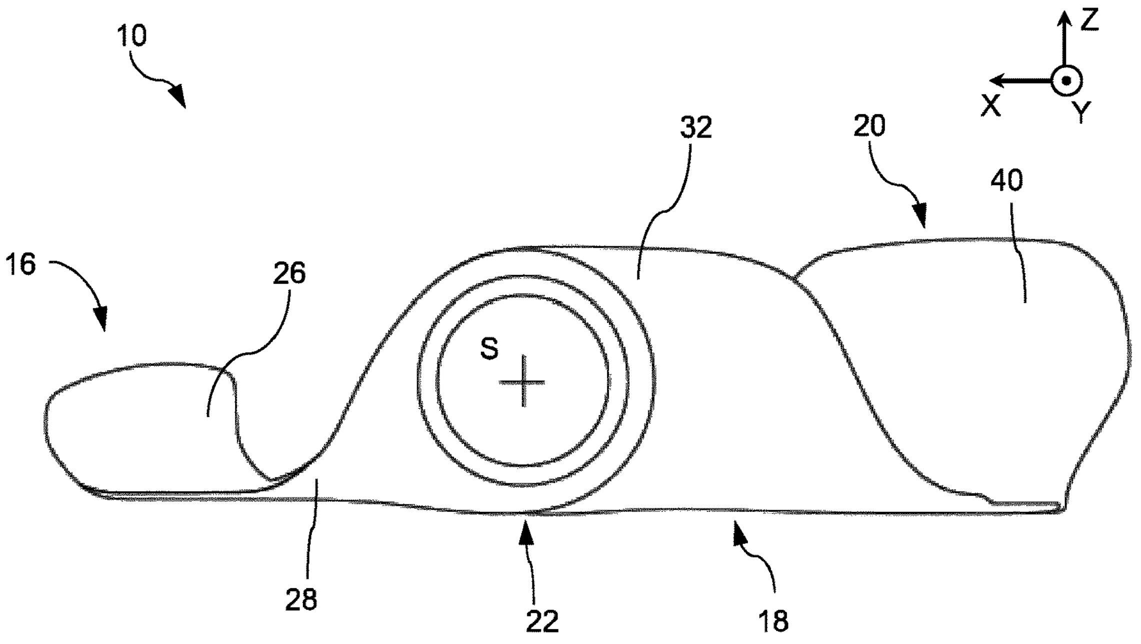
Figure 7:
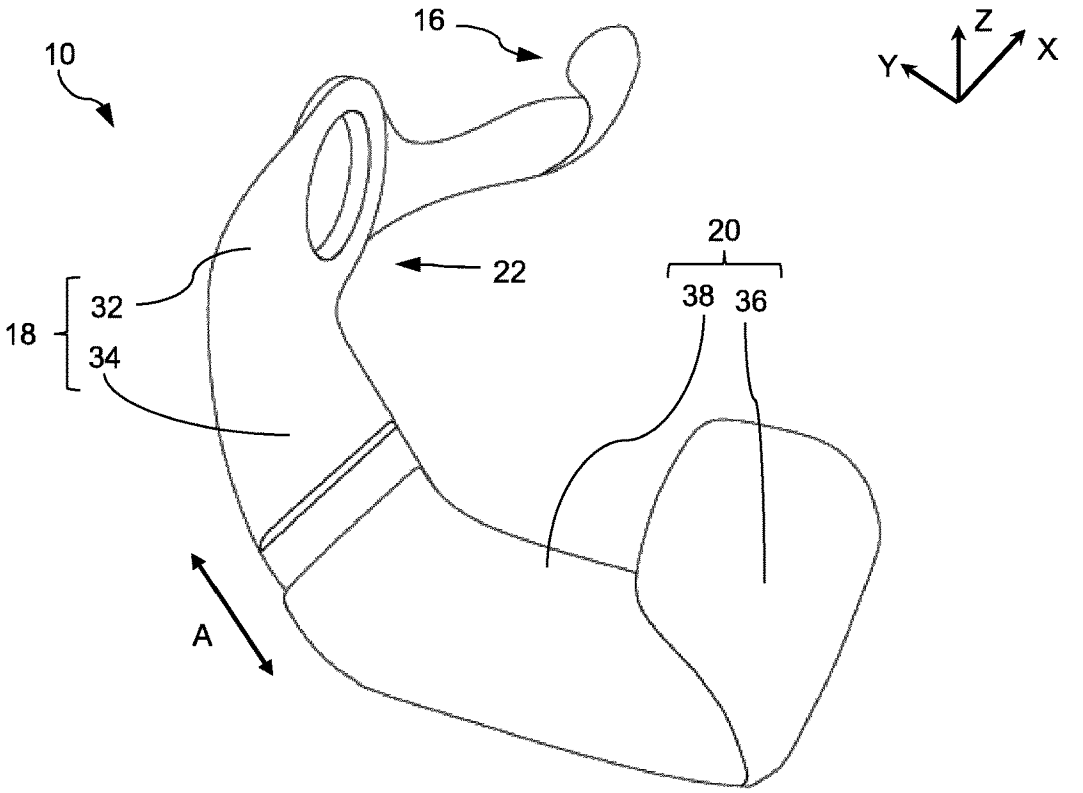

For illustrating this structural configuration of the toe splint 16, FIG. 4 shows the foot orthosis 10 in a state decoupled and disengaged from the foot, in which the toe splint 16 is arranged in its rest position. Further, by a dashed line 30, a state of the toe splint 16 is indicated in which it is arranged in the clamping position, i.e. in the fastened state. In the clamping position, an end section of the toe support section 26 is deflected and translationally displaced along the direction opposite to the first corrective force F1 by at least 0.3 cm or 0.5 cm, for example by at least 1.0 cm, with respect to the rest position.

Figure 3:
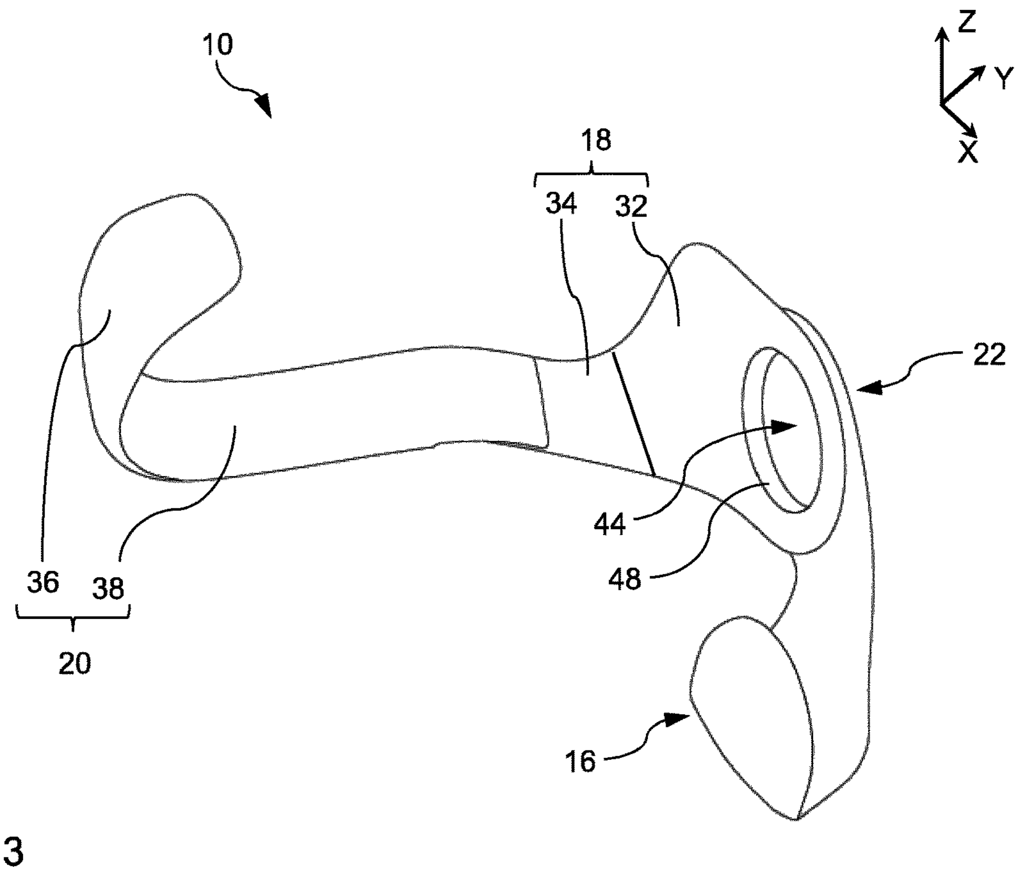

In the fastened state of the foot orthosis 10, the ball segment 18 is arranged in the region of the metatarsophalangeal joint 14 and lies against the foot in the region of the metatarsophalangeal joint 14. The ball segment 18 comprises a ball support section 32 which contacts the ball of the metatarsophalangeal joint in the fastened state of the foot orthosis 10, more specifically which contacts the ball of the metatarsophalangeal joint at a medial and plantar section. The ball segment 18 further comprises a ball base section 34, which constitutes a section of the ball segment 18 extending along the plantar surface of the foot. The ball base section 34 is integrally coupled and adhesively bonded to the ball support section 32 and arranged adjacent thereto, as indicated by a dotted line in FIG. 3.

The ball segment 18, in particular the ball support section 32, is provided in the form of a bending spring. Thus, the second corrective force F2 is provided in the form of a clamping force or bending force induced by an elastic deformation of the ball segment 18. In other words, the ball segment 18 is configured such that, in the fastened state, the ball segment 18 is arranged in a clamping position in which the ball segment is elastically deflected in a direction opposite to the second corrective force F2 with respect to a rest position in which the ball segment is arranged in a state of the foot orthosis 10 decoupled from the foot. An end section of the ball support section 32 in the clamping position can be deflected and translationally displaced by at least 0.3 cm or 0.5 cm relative to the rest position along the direction opposite to the second corrective force F2.

The ball segment 18 is connected to the metatarsal segment 20 in a force- and torque-transmitting manner. The metatarsal segment 20 is configured to be fastened to the metatarsus of the foot to be treated. Further, the metatarsal segment 20 is partially arranged opposite to the ball segment 18, in particular opposite to the ball support section 32. The metatarsal segment 20 is provided in the form of a bracket or clamp, in particular a clamping bracket, which in the fastened state of the foot orthosis 10 partially engages around a lateral metatarsal region, in particular a lateral midfoot region. The metatarsal segment 20, provided in the form of a bracket, may be configured to, in the fastened state, receive shearing forces and/or bending forces, in particular in the direction of the holding force, and to transmit these forces between the ball segment 18 and the metatarsus of the foot to be treated.

In other words, the metatarsal splint 17 is provided in the form of a bracket or clamp, in particular in the form of a bending spring or spring element, which partially engages around the metatarsus in the fastened state.

For applying the holding force to the metatarsus, the metatarsal segment 20 comprises a metatarsal support section 36 which lies against a lateral side of the metatarsus in the fastened state of the foot orthosis 10. The metatarsal support section 36 may be formed by an end section of the metatarsal segment 20. The metatarsal segment 20 further comprises a metatarsal base section 38. The metatarsal base section 38 is integrally coupled and adhesively bonded to the metatarsal support section 36 and is arranged adjacent thereto, as indicated by a dotted line in FIG. 2.

The metatarsal segment 20, in particular the metatarsal support section 36 and the metatarsal base section 38, is provided in the form of a bending spring or spring element. Thus, the holding force F3 is provided in the form of a clamping force or bending force induced by an elastic deformation of the metatarsal segment 20. In other words, the metatarsal segment 20 is configured such that, in the fastened state, the metatarsal segment 20 is arranged in a clamping position in which the metatarsal segment 20 is elastically deflected in a direction opposite to the holding force F3 with respect to a rest position of the metatarsal segment 20 in which the metatarsal segment 20 is arranged in a state of the foot orthosis 10 being decoupled from the foot. This structural configuration is illustrated in FIG. 4 by a further dashed line 44 indicating a state of the metatarsal segment 20 in which the metatarsal segment 20 is arranged in the clamping position, i.e. in the fastened state. An end section of the metatarsal support section 36 in the clamping position, with respect to its rest position, is deflected and translationally displaced along the direction opposite to the holding force F3 by at least 0.5 cm or 1.0 cm, for example 2 cm.

For fastening the foot orthosis 10 to the foot, the metatarsal splint 17 and/or the toe splint 16 optionally may be provided with bandages. For example, the toe splint 16 may use a bandage or a support band to force- and/or from-fittingly fix the toe 12 clamped in the toe splint 16 relative to the toe splint 16. For doing so, the bandage or the support band may lie against the toe 12 at least partially in its circumferential direction and may be connected to the toe splint 16. Furthermore, the metatarsal segment 20 may be provided with a second bandage or support band, which extends around the metatarsus in its circumferential direction and which is coupled to the metatarsal segment 20 at its ends in order to fix the metatarsus in the metatarsal segment 20 in a form-fitting and/or force-fitting manner.

The toe splint 16 and/or the metatarsal splint 17, in particular the ball segment 18 and/or the metatarsal segment 20, are thin-walled. In particular, the toe splint 16 and/or the ball segment 18 and/or the metatarsal segment 20 may be formed by or consist of plate-shaped and/or shell-shaped elements having a maximum thickness of less than 3 mm or 2 mm or 1 mm.

The toe splint 16, the ball segment 18 and the metatarsal segment 20 can be made of a plastic material. In particular, a plastic material may be used which is plastically deformable when being subjected to high forces, i.e. which are higher than the corrective forces F1, F2 and the holding force F3, or heat. By this configuration, the foot orthosis may be easily adapted in its geometric design to a foot to be treated. In this way, also the corrective and holding forces F1, F2, F3 induced by elastic deformation may be adapted.

According to a further development, at least one of the support sections 26, 32, 36 may have a lower stiffness, in particular against shearing and/or bending forces in direction of the first or second corrective force F1, F2, compared to the base section 28, 34, 38 arranged adjacent thereto. Specifically, the at least one support section 26, 32, 36 may be made of a material which has a lower modulus of elasticity or a lower hardness, for example a lower Shore hardness, compared to the material of the adjacent base element 28, 34, 38.

Figure 8:
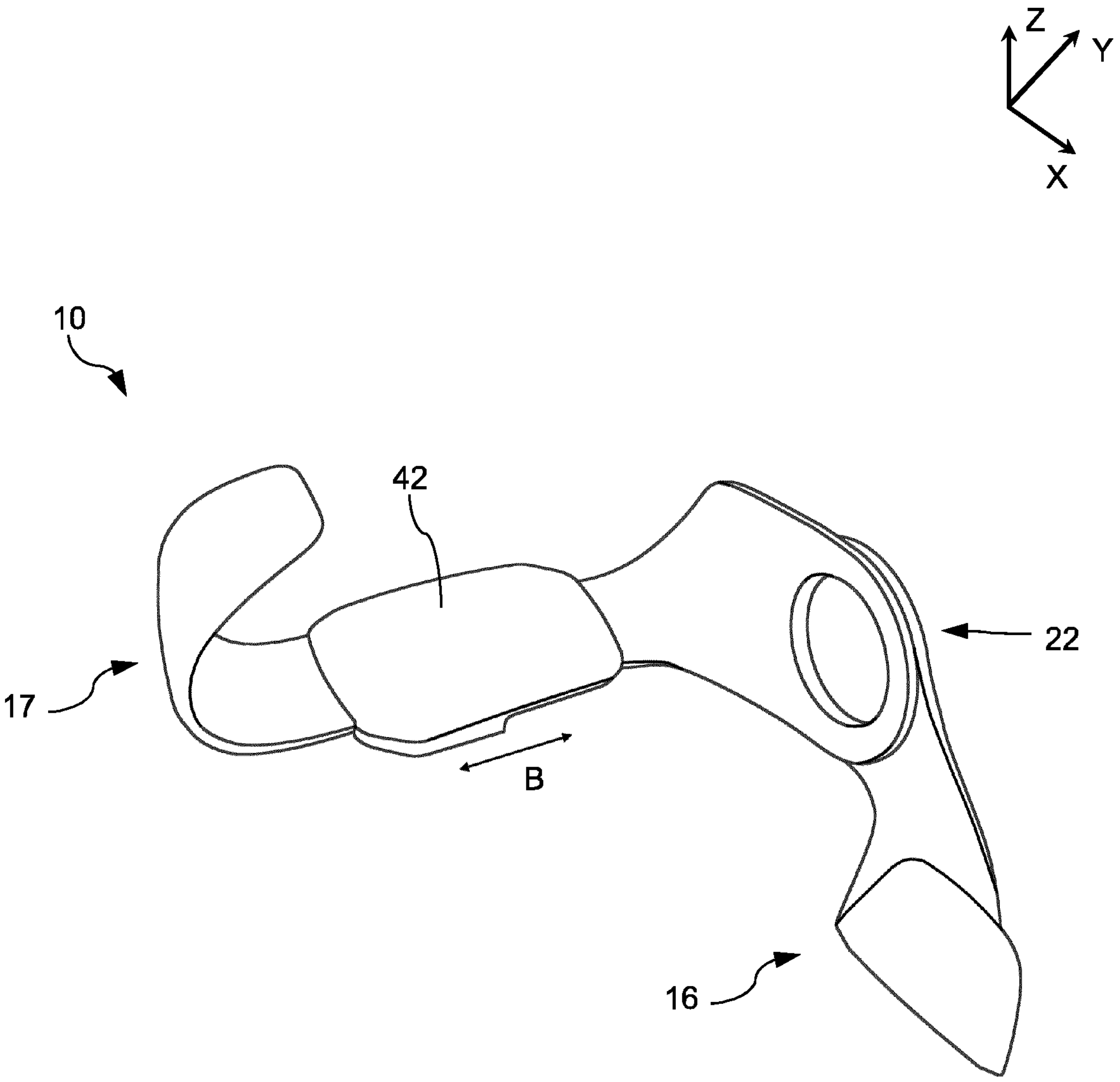

As depicted in FIG. 8, the ball base section 34 and the metatarsal base section 38 are coupled to each other such that they are translationally displaceable relative to each other along an axis that is in a plane with, but transverse to the longitudinal axis X and a transverse axis Y of the foot orthosis 10, as indicated by arrow A in FIG. 8. In other words, the two sections 34, 38 are translationally displaceable relative to each other along the longitudinal axis X and the transverse axis Y of the foot orthosis 10. The foot orthosis 10 is configured such that the two sections 34, 38 can be fixed in a desired position relative to each other in a force-fitting and/or form-fitting manner.

Optionally, the foot orthosis 10 may further comprise a foot cushion 42 which is configured to be releasably coupled to the ball base section 34 and/or the metatarsal base section 38 and is displaceable relative thereto in order to arrange the foot cushion 42 in a patient-specific manner, as indicated by arrow B in FIG. 8.

As set forth above, the toe splint 16 and the metatarsal splint 17 are pivotably coupled relative to each other by means of the swivel joint 22 about the swivel axis S. The swivel joint 22 is adapted to transmit bending forces parallel to the first or the second corrective force F1, F2 between the metatarsal splint 17 and the toe splint 16 in the state of the foot orthosis 10 fastened to the foot, wherein the first corrective force F1, the second corrective force F2, and the holding force F3 are provided in the form of a bending force induced by an elastic deformation of the toe splint 16 and the metatarsal splint 17.

For interacting with the metatarsophalangeal joint 14 of the foot to be treated, i.e. for exerting the second corrective force F2, the foot orthosis 10 is equipped with the swivel joint 22. The configuration of the swivel joint 22 is specified below with reference to FIG. 9, which shows a longitudinal section along the swivel axis S through the swivel joint 22.

Figure 9:
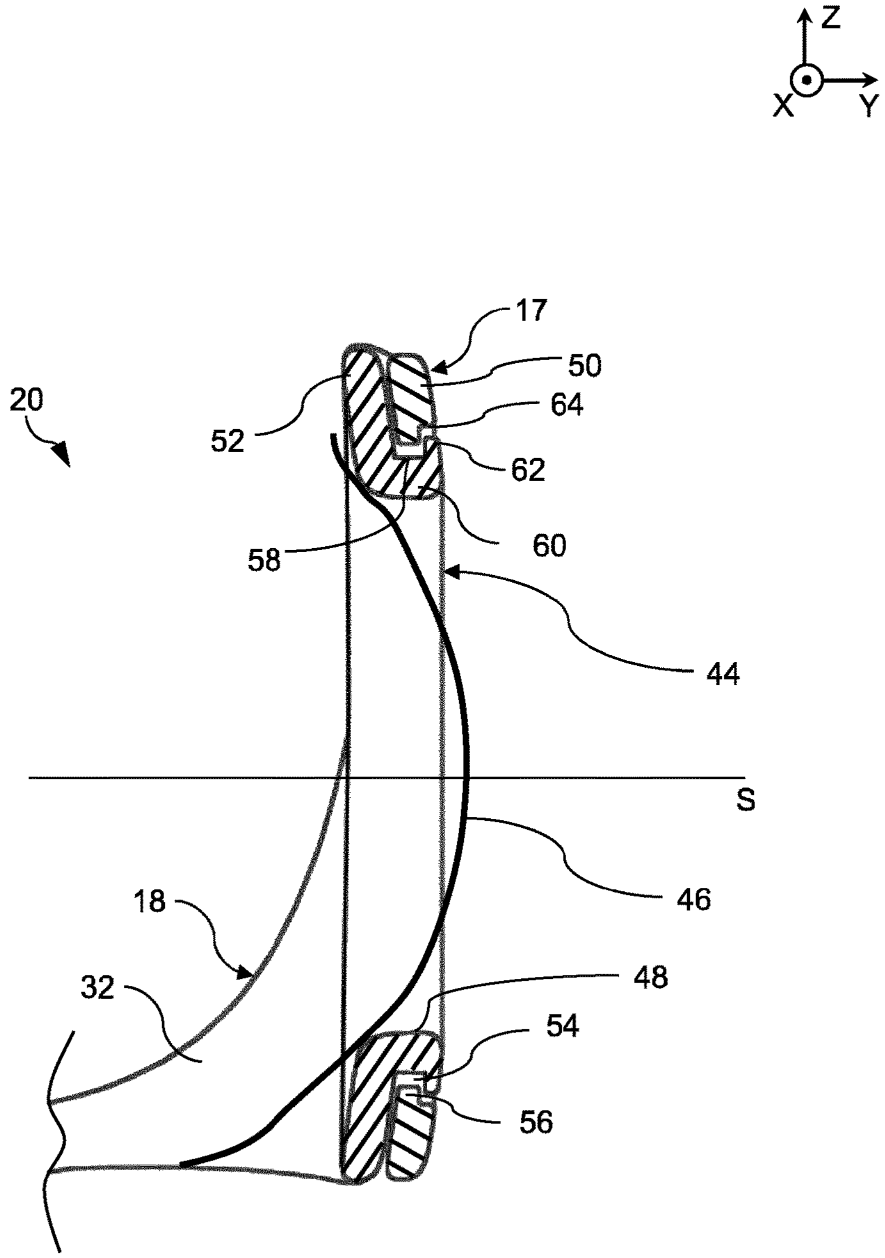
FIG. 9 longitudinal section of a swivel joint of the foot depicted in FIGS. 1 to 8.

As can be gathered from FIG. 9, the swivel joint 22 is provided with a recess 44 along its swivel axis S and is designed such that, when the foot orthosis 10 is fastened to the foot, a sideways protruding section 46 of the metatarsophalangeal joint 14 is at least partially received in the recess 44. This is illustrated in FIG. 9 by a dashed line indicated by reference numeral "46". The sideways protruding section 46 of the metatarsophalangeal joint 14 may be or form a pseudoexostosis.

The swivel joint 22 is a hollow trunnion swivel joint. In other words, the components forming the swivel joint 22 are designed to be hollow along the swivel axis S such that the swivel joint 22 is provided with the recess 44 around and along its swivel axis S. The swivel joint 22 is designed such that, in the fastened state of the foot orthosis 10, the swivel joint 22 is arranged on the foot and the metatarsophalangeal joint 14 such that the swivel joint 22 is arranged circumferentially around the sideways protruding section 46 of the metatarsophalangeal joint 12, for example around a pseudo-exostosis, wherein the sideways protruding section 46 of the metatarsophalangeal joint 14 at is arranged least partially in the recess of the swivel joint 22.

The recess 44 is provided in the form of a through hole or opening extending along the swivel axis S. The swivel joint 22 is designed such that, in the fastened state, the sideways protruding section 46 of the metatarsophalangeal joint extends along at least 50% or at least 70% or at least 80% of the maximum width or thickness of the swivel joint 22. In the shown embodiment, the sideways protruding section 46 of the metatarsophalangeal joint 14 protrudes through the recess 44 along the swivel axis S. The swivel joint has a maximum width along the swivel axis S, i.e. along the transverse axis Y, of at most 1.0 cm or 0.6 cm.

The swivel joint 22 comprises a sidewall 48 which delimits the recess 44 and which is arranged circumferentially around the swivel axis. The sidewall 48 has a minimum radius of curvature of 1 mm or 2 mm or 5 mm.

The recess 44 has a minimum diameter along a direction transverse to the swivel axis S of at least 1.5 cm or at least 2.0 cm or at least 2.5 cm. More specifically, in the shown configuration, the diameter is substantially 3.0 cm.

In the shown configuration, the swivel axis S of the swivel joint 22 is arranged in alignment, i.e. coincides, or substantially in alignment with the flexion-extension joint axis of the metatarsophalangeal joint 14. The flexion-extension joint axis is understood to be the joint axis about which the toe 12 is pivoted relative to the metatarsus during flexion and extension movements. This is achieved by arranging the swivel joint 22 on the medial side of the foot in the fastened state. Specifically, the swivel joint 22 is designed such that relative pivotal movement between the toe splint 16 and the metatarsal splint 17 is permitted or released only about the swivel axis S.

As can be gathered from FIG. 9, the swivel joint 22 is constituted by at least two components, but is not limited to this configuration and in alternative embodiments may be constituted by more than two components.

In particular, the swivel joint 22 comprises a first joint element 50 coupled to the toe splint 16, in particular integrally coupled or adhesively bonded thereto, and a correspondingly designed second joint element 52 which is engaged with the first joint element 50 and which is coupled to the metatarsal splint 17, in particular the ball segment 18, in particular integrally connected or adhesively bonded thereto. Specifically, the first joint element 50 may be formed by an end section of the toe base section 28 and the second joint element 52 may be formed by an end section of the ball support section 32. In the fastened state, the second joint element 52 is arranged, along the swivel axis S, between the foot and the first joint element 50.

In the shown configuration, the first joint element 50 is provided in the form of a joint ring. The second joint element 52 is provided in the form of a hollow joint pin on which the joint ring, i.e. the first joint element 50, is guided along a guiding surface. The first and the second joint element 50, 52 are designed and are in engagement in such a way that they are form-fittingly coupled along the swivel axis S and transversely thereto.

For doing so, the second joint element 52 is provided with a receiving groove 54 which extends circumferentially around the swivel axis S and is engaged with a complementary designed connecting ring 56 of the first joint element 50. The receiving groove 54 further extends in radial direction relative to the swivel axis S such that the receiving groove 54 is delimited in both axial directions along the swivel axis S and comprises an opening in radial outward direction. Via the opening, the connecting ring 56 protrudes into the receiving groove 54. In other words, in a longitudinal section along the swivel axis S, the receiving groove 54 has a substantially U-shaped contact or sliding surface 58, also referred to as guiding surface, for the connecting ring 56. Thus, the receiving groove 54 and the connecting ring 56 are form-fittingly engaged in both directions along the swivel axis S. By this configuration, the connection between the first and the second joint element 50, 52 can be effectively prevented from being unintentionally released and, at the same time, a simple and robust design of the joint unit may be ensured. Alternatively, the first joint element may be provided with a receiving groove and the second joint element may be provided with a correspondingly designed connecting ring.

The swivel joint 22 is designed and configured such that, in the fastened state of the foot orthosis 10, the second joint element 52 is arranged between the foot and the first joint element 50, wherein a connecting stud 60 of the second joint element 52, which forms the receiving groove 54, circumferentially delimits the recess 44 in radial direction. The connecting stud 60 extends along the swivel axis S such that the connecting stud 60 overlaps the first joint element 50 in axial direction of the swivel joint 22 i.e. along the swivel axis S. Specifically, the connecting stud 60 engages around the connecting ring 56. An end portion 62, which laterally delimits the recess 44 at, is arranged in a further recess 64 in the first joint element 50, wherein the further recess 64 is located sideways on the outside of the first joint element 50. By this configuration, a flushed outer surface of the swivel joint 22 is achieved.

Figure 10:
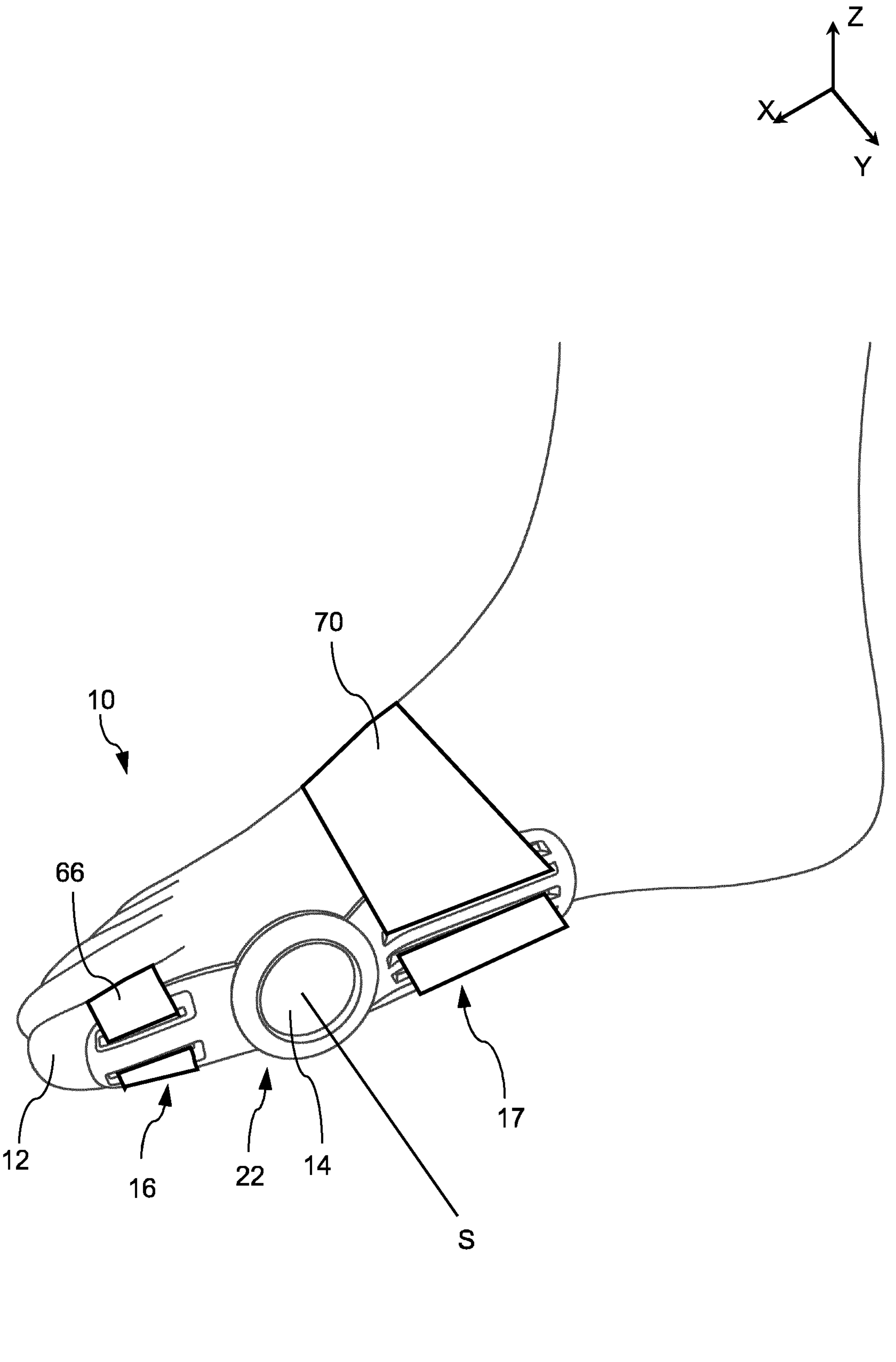
FIG. 10 a perspective view of the foot orthosis according to a further embodiment, in which the foot orthosis is fastened to the patient's foot.
Figure 11:
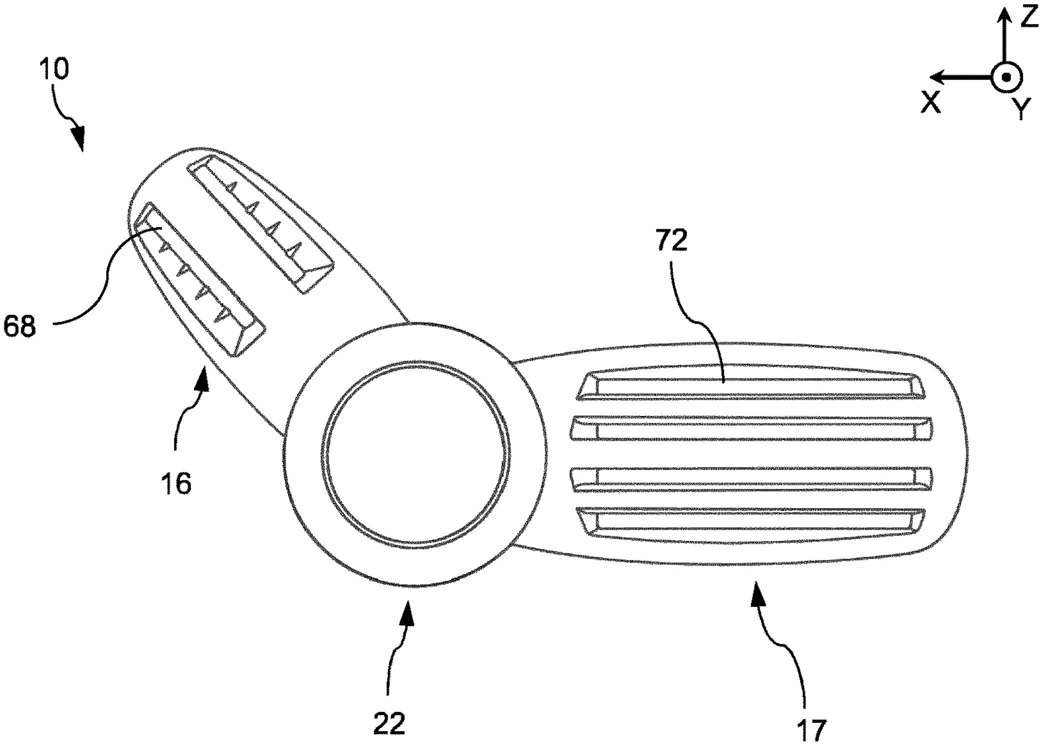
FIGS. 11 and 12 the foot orthosis depicted in FIG. 10 in a state decoupled from the foot.
Figure 12:
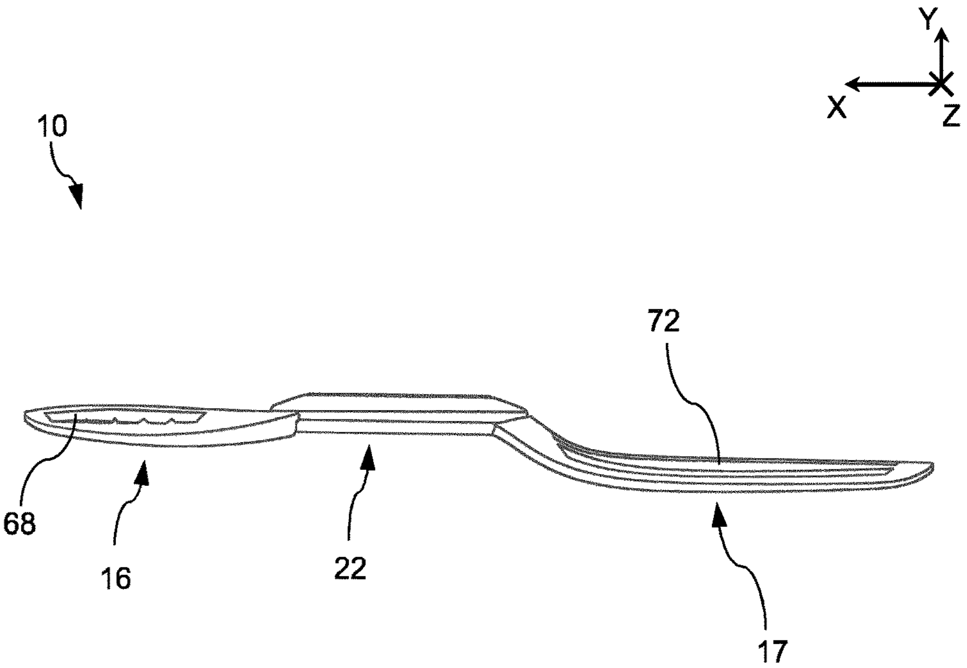

FIGS. 10 to 12 show a further embodiment of the foot orthosis 10 that differs from the embodiment shown in FIGS. 1 to 9 in particular in the configuration and arrangement of the toe splint 16 and the metatarsal splint 17. The design of the swivel joint 22, specifically of the first and the second joint element 50, 52, corresponds to the design of the swivel joint 22 as shown in FIG. 9 and as described in the context of the above embodiment.

FIG. 10 shows the foot orthosis 10 in a state fastened to the foot. The toe splint 16 comprises a toe limb extending along the inner side of the toe in the form of a bracket element and a first support band 66 coupled thereto in the form of a bandage. The first support band 66 is guided around the toe 12 along its circumferential direction and is connected to the toe limb at its ends so as to form- and/or force-fittingly fix the toe limb relative to the toe 12. As such, the toe limb forms a bending spring that is attachable to the toe 12 by means of the first support band 66. The toe limb comprises coupling elements 68, via which end sections of the first support band 66 are force-fittingly connected to the toe limb. In the shown configuration, the coupling elements 68 are provided in the form of slit openings through which the first support band 66 is guided when wrapped around the toe 12 so as to fix the foot orthosis 10 to the foot to be treated and accordingly to apply the first corrective force to the foot via the first support band 66.

The metatarsal splint 17 comprises a metatarsal limb in the form of a bracket element extending along the inner side of the foot and a second support band 70 coupled thereto in the form of a bandage. The second support band 70 is guided around the metatarsus along its circumferential direction and is connected at its ends to the metatarsal limb so as to form- and/or force-fittingly fix the metatarsal limb relative to the metatarsus. As such, the metatarsal limb forms a bending spring which is attachable to the metatarsal by means of the second support band 70. The metatarsal limb comprises further coupling elements 72, via which end sections of the second support band 70 are force-fittingly connected to the metatarsal limb. In the shown configuration, the further coupling elements 72 are provided in the form of slit openings through which the second support band 70 is guided when being wrapped around the metatarsus so as to fix the foot orthosis 10 to the foot to be treated and accordingly to apply the holding force to the foot via the second support band 70.

FIGS. 11 and 12 show the foot orthosis 10 in a state decoupled from the foot, in which the support bands 66, 70 are not shown for overview reasons.

Accordingly, the swivel joint 22 is configured to transmit bending forces parallel to the first and the second corrective force F1, F2 between the metatarsal splint 17 and the toe splint 16 when the foot orthosis 10 is fastened to the foot, wherein the first corrective force F1, the second corrective force F2 and the holding force F3 are provided in the form of a bending force induced by an elastic deformation of the metatarsal splint 16, specifically the toe limb, and the metatarsal splint 17, specifically the metatarsal limb.

Where applicable, all of the individual features illustrated in the above embodiments can be combined and/or interchanged without departing from the scope of the invention.

LIST OF REFERENCE SIGNS

10 foot orthosis
12 big toe
14 metatarsophalangeal joint
16 toe splint
17 metatarsal splint
18 ball segment
20 metatarsal segment
22 swivel joint
24 contact surface
26 toe support section
28 toe base section
30 clamping position of the toe splint
32 ball support section
34 ball base section
36 metatarsal support section
38 metatarsal base section
40 clamping position of the metatarsal splint
42 foot cushion
44 recess
46 sideways protruding section of the metatarsophalangeal joint
48 sidewall
50 first joint element
52 second joint element
54 receiving groove
56 connecting ring
58 contact or sliding surface
60 connecting stud
62 end section
64 further recess
66 first support band
68 coupling element
70 second support band
72 further coupling element
F1 first corrective force
F2 second corrective force
F3 holding force
S swivel axis.

The invention claimed is:

1. A foot orthosis for correcting foot malpositions comprising a toe splint configured to be fastened to a toe and a metatarsal splint configured to be fastened to a metatarsal region of the foot, each of which are pivotably connected relative to one another by means of a swivel joint, wherein in a fastened state in which the foot orthosis is fastened to the foot, the foot orthosis is configured to exert a first corrective force on the toe via the toe splint and to exert a second corrective force on a metatarsophalangeal joint via the swivel joint in the opposite direction to the first corrective force; in the fastened state, the foot orthosis is configured to exert a holding force on the metatarsus via the metatarsal splint which is directed opposite to the second corrective force;

the swivel joint is provided with a recess in the form of a through hole which extends along a swivel axis of the swivel joint and which is designed such that, in the state fastened to the foot, a sideways protruding section of the metatarsophalangeal joint is received in the through hole, wherein the swivel joint comprises a first joint element in the form of a joint ring connected to the toe splint and a second joint element in the form of a joint pin connected to the metatarsal splint which are form-fittingly engaged along and transversely to the swivel axis of the swivel joint, wherein the joint pin is provided with a receiving groove in which a correspondingly designed connecting ring of the joint ring is guided, the joint pin comprises a circumferential radial shoulder which provides a form-fit connection between the joint ring and the joint pin in direction of the swivel axis and which is received in a correspondingly designed further recess of the joint ring; the swivel joint is configured to, in the fastened state, transmit bending forces between the metatarsal splint and the toe splint which are parallel to the first or second corrective force; and in the fastened state, the foot orthosis is configured such that the first corrective force, the second corrective force and the holding force are provided in the form of a bending force induced by an elastic deformation of the toe splint and the metatarsal splint.

2. The foot orthosis of claim 1, wherein the swivel joint comprises a hollow trunnion swivel joint.

3. The foot orthosis of claim 1, wherein the swivel joint has a maximum width along the swivel axis of not more than 0.6 cm.

4. The foot orthosis of claim 1, wherein, in the fastened state of the foot orthosis, the sideways protruding section of the metatarsophalangeal joint extends along at least 50% of the maximum width of the swivel joint along the swivel axis.

5. The foot orthosis of claim 1, wherein, in the fastened state of the foot orthosis, the sideways protruding section of the metatarsophalangeal joint protrudes through the through hole, along the swivel axis.

6. The foot orthosis of claim 1, wherein the swivel joint is configured to include a sidewall of the swivel joint that delimits the recess and has a minimum radius of curvature of 1 mm to 5 mm.

7. The foot orthosis of claim 6, wherein the swivel joint is configured to include a sidewall of the swivel joint that delimits the recess and has a minimum radius of curvature of 1 mm to 2 mm.

8. The foot orthosis of claim 6, wherein the swivel joint is configured to include a sidewall of the swivel joint that delimits the recess and has a minimum radius of curvature of 5 mm.

9. The foot orthosis of claim 1, wherein a minimum diameter of the recess about the swivel axis is at least 1.5 cm.

10. The foot orthosis of claim 1, wherein in the fastened state of the foot orthosis, the swivel axis of the swivel joint substantially coincides with a base joint axis of the metatarsophalangeal joint of the toe.

11. The foot orthosis of claim 10, wherein the swivel joint is configured such that a relative pivoting movement between the toe splint and the metatarsal splint is released about the swivel axis.

12. The foot orthosis of claim 1, wherein the swivel joint comprises a first joint element connected to the toe splint, and a second joint element connected to the metatarsal splint.

13. The foot orthosis of claim 12, wherein in the fastened state, the second joint element connected to the metatarsal splint is arranged, along the swivel axis, between the foot and the first joint element connected to the toe splint.

14. The foot orthosis of claim 12, wherein the first joint element of the swivel joint is integrally or adhesively connected to the toe splint, and the second joint element is integrally or adhesively connected to the metatarsal splint.

15. The foot orthosis of claim 1, wherein the swivel joint has a maximum width along the swivel axis of not more than 1.0 cm.

* * * * *